(12) United States Patent
Merritt

(10) Patent No.: US 11,040,017 B2
(45) Date of Patent: Jun. 22, 2021

(54) CANNABIDIOL FORMULATION

(71) Applicant: Healthy Roots Inc., Portland, OR (US)

(72) Inventor: Elizabeth Merritt, Vancouver, WA (US)

(73) Assignee: Healthy Roots Inc., Portland, OR (US)

( * ) Notice: Subject to any disclaimer, the term of this patent is extended or adjusted under 35 U.S.C. 154(b) by 0 days.

(21) Appl. No.: 16/556,149

(22) Filed: Aug. 29, 2019

(65) Prior Publication Data

US 2020/0138736 A1 May 7, 2020

Related U.S. Application Data

(60) Provisional application No. 62/756,458, filed on Nov. 6, 2018.

(51) Int. Cl.
| | | |
|---|---|---|
| *C07C 35/21* | (2006.01) | |
| *A61K 31/05* | (2006.01) | |
| *A61K 36/185* | (2006.01) | |
| *A61K 31/353* | (2006.01) | |

(52) U.S. Cl.
CPC ............ *A61K 31/05* (2013.01); *A61K 31/353* (2013.01); *A61K 36/185* (2013.01)

(58) Field of Classification Search
CPC .................................................... C07C 35/21
See application file for complete search history.

(56) References Cited

U.S. PATENT DOCUMENTS

2018/0133272 A1* 5/2018 Crowley ................ A61K 31/05

OTHER PUBLICATIONS

Green Roads, CBD Oil, posted at greenroadsworld.com, 2019 © Green Roads, [online], [site visited Nov. 19, 2019], 12 pages, available from Internet, <URL: https://www.greenroadsworld.com/products/cbd-hemp-oil-100mg/>.
Extract Labs, CBD Tincture, posted at extractlabs.com, © Extract Labs 2019, [online], [site visited Nov. 19, 2019], 8 pages, available from Internet, <URL: https://www.extractlabs.com/product/original-cbd-tincture/>.
PureKana, CBD Gummies, posted at purekana.com, © 2019 PureKana, [online], [site visited Nov. 19, 2019], 4 pages, available from Internet, <URL: https://purekana.com/collections/cbd-gummies/>.
Green Nectar, Full Spectrum Oil, posted at ordergn.com, © 2019 Green Nectar, [online], [site visited Nov. 19, 2019], 4 pages, available from Internet, <URL: https://ordergn.com/menu/cotc-fso-full-spectrum-oil-cbd-thc/>.
Extract Labs, CBD Isolate, posted at extractlabs.com, © Extract Labs 2019, [online], [site visited Nov. 19, 2019], 8 pages, available from Internet, <URL: https://www.extractlabs.com/product/cbd-isolate/>.

* cited by examiner

*Primary Examiner* — Rosanne Kosson
(74) *Attorney, Agent, or Firm* — Howard Russell

(57) ABSTRACT

Cannabidiol (CBD) formulation comprising a mixture of full spectrum cannabidiol oil (FSO) and cannabidiol isolate (CBD isolate) is disclosed. The formulation contains a total amount of CBD derived from a combination of an amount of CBD in the FSO and an amount of CBD from the CBD isolate. The formulation of FSO and CBD isolate in used for medicinal and health benefits in a wide range of products, such as tinctures, capsules, creams or lotions, bath salts or bombs, soaps, pet or animal tinctures, and pet or animal edible chews.

17 Claims, 3 Drawing Sheets

100 – THC

105 – THCA

110 – CBD

115 – CBDA

120 – CBG

125 – CBGA

130 – CBC

135 – CBCA

140 – CBN

145 – THCV

200 – Isoprene

205 – α-Pinene

210 – β-Pinene

215 – Δ³-Carene

220 – d-Limonene

225 – Camphene

230 – Myrcene

235 – β-Phellandrene

240 – Sabinene

245 – α-Terpinene

250 – Ocimene

255 – α-Thujene

260 – Terpinolene

265 – Terpinene

CANNABIDIOL FORMULATION

REFERENCE TO RELATED APPLICATIONS

The present Patent Application claims the priority and benefit of U.S. Provisional Patent Application Ser. No. 62756458 to Elizabeth Merritt, for Cannabidiol Formulation, filed 6 Nov. 2018.

FIELD OF THE INVENTION

The invention relates to a formulation of cannabidiols produced from hemp full spectrum oil and cannabidiol isolate.

BACKGROUND OF THE INVENTION

Phytocannabinoids or cannabinoids are increasingly being recognized for their health and medicinal effects. There are about 120 different cannabinoids that are naturally occurring in many plant species. Cannabinoid compounds have been shown to inhibit inflammation and lessen water retention, have antimicrobial effects, and play a protective role in many liver processes. These compounds also have been described as a potential target for the treatment of atherosclerosis and osteoporosis. In the gastrointestinal tract cannabinoids have been shown to play a significant role in reducing inflammation. Consequently, such cannabinoids are potential drug candidates for the treatment of a range of different diseases.

Cannabinoids for consumption or pain-relieving applications are most commonly obtained from plants of the species Cannabis Sativa, which includes both industrial hemp and marijuana. While of the same species, these plants have a very different genetic profile. Industrial Hemp is a strain of Cannabis sativa, while marijuana can be a strain of Cannabis sativa, Cannabis indica, or Cannabis ruderalis. Industrial hemp and marijuana differ significantly in their cannabinoids profile. Industrial hemp has a high amount of the beneficial, pain-relieving cannabinoid cannabidiol (CBD) and only trace amounts of the cannabinoid tetrahydrocannabinol (THC). Conversely, marijuana in almost all varieties has low levels of CBD and relatively high levels of THC, which is the main psychotropic compound in marijuana. The cannabinoid profile of hemp is preferable for people wishing to obtain benefits from cannabis without the psychotropic effects of marijuana. Hemp has a number of uses, including use for making herbal supplements, food, fiber, rope, paper, bricks, oil, natural plastic, and other products.

CBD from hemp for medical and health benefits is typically available for oral consumption or topical application in the forms of tinctures, capsules, creams or lotions, balms, and so on. CBD is extracted from hemp plants and is typically provided to users in the form of a full spectrum hemp oil or highly purified, isolated CBD. Full spectrum hemp oil contains dozens of cannabinoids. CBD is the most abundant cannabinoid in full spectrum hemp oil, in which CBD makes up to over 90% of the cannabinoid content. CBD isolate contains up to 99.9% CBD as a powder that can be mixed into a number of carriers for different oral and topical applications.

Full spectrum hemp oil (FSO) and CBD isolate each have advantages and disadvantages. FSO not only contains CBD, but also an array of cannabinoids and other natural constituents that can work together to provide medicinal and health benefits beyond that offered by CBD isolate. The complex mix of cannabinoids, essential nutrients, protein, and healthy fats in FSO can provide pain relief and promote good health. FSO has the drawback of containing levels of THC 100, up to 0.3% or more, that deters some from using FSO. In addition, many users find FSO to have an unpleasant taste, and therefore are reluctant to take it. CBD advantageously is responsible for a large bulk of the therapeutic qualities of hemp oil, and has no psychotropic effects since it contains essentially no THC. Pure CBD can be readily mixed into formulations for oral consumption with little to no undesirable taste from the CBD isolate. While CBD is beneficial for medical and health uses when isolated from the rest of the compounds found in cannabis, it may not be as beneficial without the other cannabinoids and terpenes in cannabis, which collectively provide the "entourage effect."

Despite the advantages of readily available FSO and CBD isolate products, there remains a need in the art for beneficial, improved CBD formulations that suffer from, or suffer much less from, the drawbacks of FSO or CBD isolate. In particular, there is a need for CBD formulations that offer the medicinal and health benefits of FSO and CBD isolate without an undesirable taste or other drawbacks that might be associated with either FSO or CBD isolate. The present invention provides such desirable CBD formulations.

SUMMARY OF THE INVENTION

Novel formulations containing cannabidiol (CBD) and other cannabinoids are disclosed herein. The presently disclosed CBD formulations include a novel combination of full spectrum hemp oil (FSO) and CBD isolate. The amount of desired CBD in these formulations is obtained from the contribution of CBD from FSO and CBD isolate. These formulations provide the benefits of FSO and its array of cannabinoids along with CBD isolate while reducing the amount of THC found in FSO alone. In addition, these CBD formulations have an improved taste compared to FSO alone, making them more desirable for oral consumption of CBD and other cannabinoids.

The amount of CBD in the FSO and CBD isolate of the present formulations is determined by analytical testing, preferably high performance liquid chromatography. The total, 100% amount of CBD in a particular formulation that is contributed by the FSO and CBD isolate ranges from a low of 55% CBD from FSO and high of 45% CBD from CBD isolate, to a high of 80% CBD from FSO and a low of 20% CBD from CBD isolate, according to this disclosure.

The formulations of FSO and CBD isolate have levels of THC that range from less than 0.15% THC to a maximum level of less than 0.3% THC.

The CBD formulations of combined FSO and CBD isolate are used in a wide range of oral and topical applications that include products, but are not limited to, tinctures, capsules, creams or lotions, balms, bath salts or bombs, and pet products such as tinctures and edible chews.

DETAILED DESCRIPTION OF THE INVENTION

The present embodiments relate to novel CBD formulations that combine hemp FSO with CBD isolate. These formulations advantageously provide the medical and health benefits of FSO and those obtained with particular overall levels of CBD in a given formulation. Unless otherwise stated all percentages given herein are percent weight (wt.).

Figure 1:
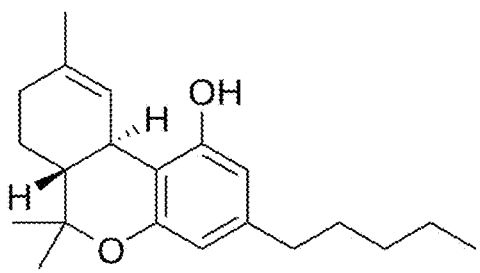
FIG. 1 shows some of the various, naturally occurring cannabinoids which are likely to be found in FSO.
Figure 1:
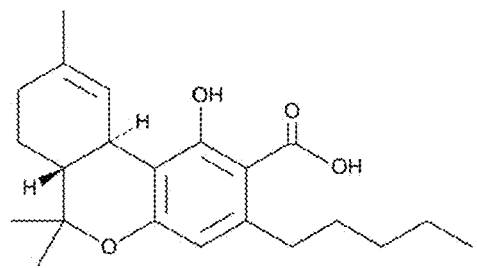
Figure 1:
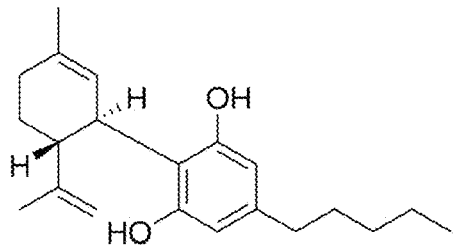
Figure 1:
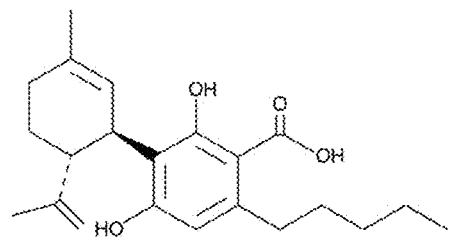
Figure 1:
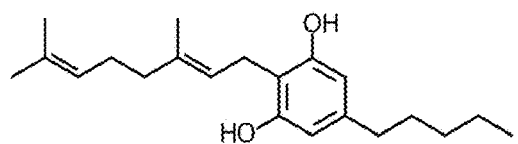
Figure 1:
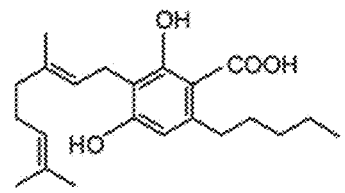
Figure 1:
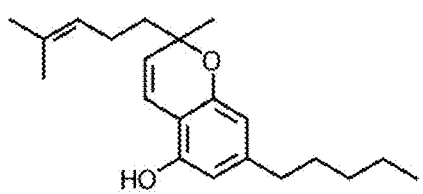
Figure 1:
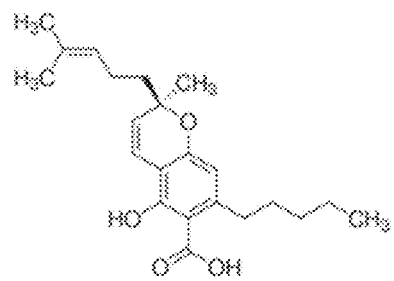
Figure 1:
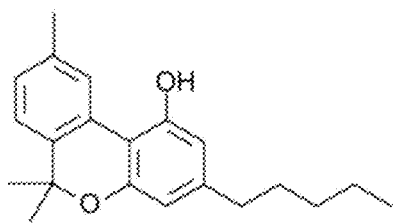
Figure 1:
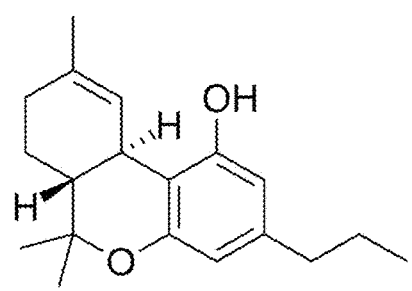
Figure 2:
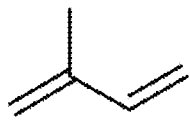
FIG. 2 shows some of the various, naturally occurring terpenes which are likely to be found in FSO.
Figure 2:
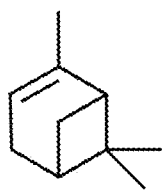
Figure 2:
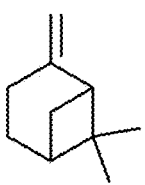
Figure 2:
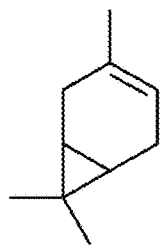
Figure 2:
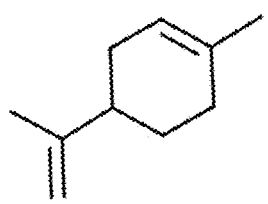
Figure 2:
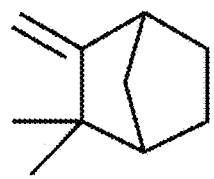
Figure 2:
Figure 2:
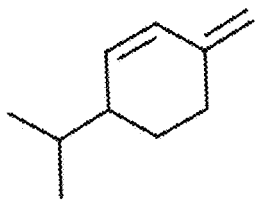
Figure 2:
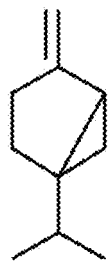
Figure 2:
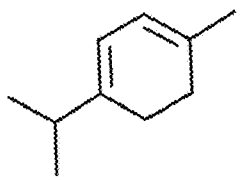
Figure 2:
Figure 2:
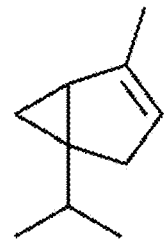
Figure 2:
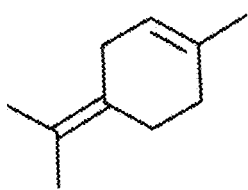
Figure 2:
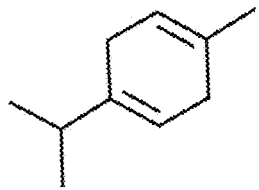

As used herein, FSO refers to a hemp oil that contains a full spectrum of cannabinoids, terpenes, flavonoids and other beneficial compounds that are found in industrial hemp plants. Naturally occurring cannabinoids and terpenes found in cannabis are shown in FIGS. 1 and 2. Major cannabinoid constituents in FSO besides CBD include, but are not limited to, cannabidiolic acid (CBDA) 115, cannabichromene (CBC) 130, cannabigerol (CBG) 120, cannabidivarin (CBDV), and cannabinol (CBN) 140. Examples of lesser known cannabinoids include, but are not limited to, cannabicyclol (CBL), cannabitriol (CBT), cannabicitran (CBT), and cannabifuran (CBF). Each of these cannabinoids are non-psychoactive. FSO also contains the carboxyl forms of many of these cannabinoids including THCA 105, CBGA 125, and CBCA 135. FSO also contains terpenes such as isoprene 200, α-pinene 205, β-pinene 210, $\Delta^3$-carene 215, d-limonene 220, camphene 225, myrcene 230, β-phellandrene 235, sabinene 240, α-terpinene 245, ocimene 250, α-Thujene 255, terpinolene 260, and terpinene 265. FSO also contains numerous other constituents, such as amino acids, carbohydrates, vitamins, fatty acids, trace minerals (including iron, zinc, calcium, magnesium, potassium), beta-carotene, flavonoids, ketones, nitrogenous compounds, alkanes, glycosides, and pigments. Because of the similarity between THC 100, THCA 105, and other cannabinoids, as well as the non-polar nature of cannabinoids and the terpenes, separation of the psychoactive components from the other cannabinoids and terpenes is difficult.

Figure 3:
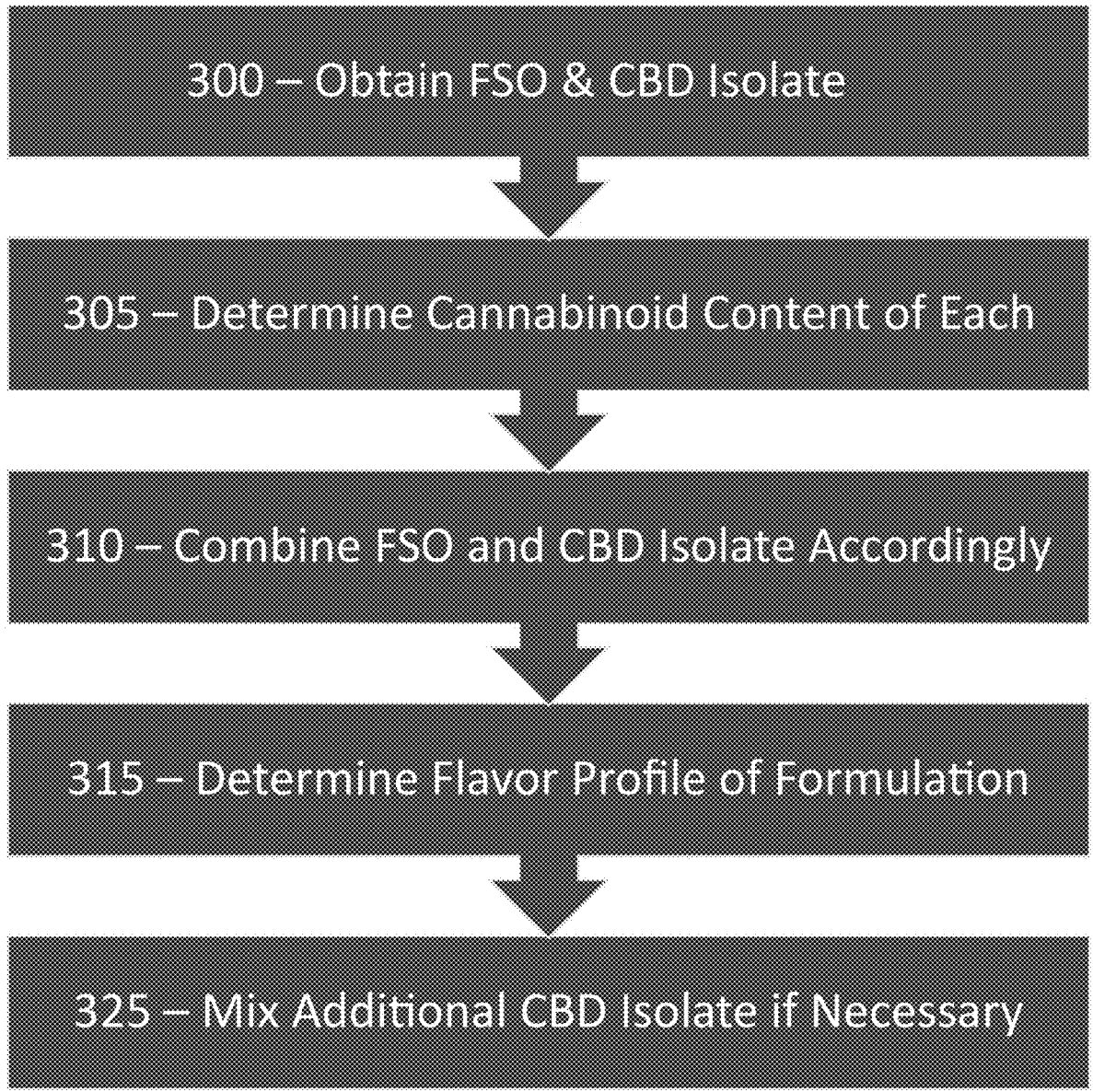
FIG. 3 shows a process by which a novel CBD formulation of a present embodiment may be produced.

FIG. 3 illustrates a process by which FSO and CBD Isolate may be combined to produce a novel high potency CBD formulation which provides the entourage effect associated with various cannabinoids and terpenes, while minimizing the THC content and poor taste associated with FSO, among other benefits. CBD for use in such CBD formulations herein may be obtained from industrial hemp Cannabis Sativa strains by any of a number of extraction processes known in the art 300. Applicable commonly used extraction methods include, but are not limited to, solvent extraction using alcohols (such as ethanol, isopropanol), hydrocarbons (such as butane, hexane, pentane) and supercritical carbon dioxide ($CO_2$), as well as thermal extraction processes. Virtually any extraction method that produces FSO from industrial hemp may be applicable for producing FSO used in the presently disclosed formulations. In preferred embodiments, FSO is extracted from industrial hemp with ethanol or carbon dioxide, using methodologies that are well known in the art. FSO contains cannabinoids that have been extracted and concentrated. Accordingly, prior to dilution for use in a final formulation, the FSO typically will contain THC in excess in a range of about 2-3% total THC content. The FSO is accordingly diluted in a final formulation to have the desired amounts of CBD and THC, as indicated herein.

CBD isolate that is used in the presently disclosed CBD formulations is obtained from FSO 300. CBD isolate is obtained from FSO by separating it from other cannabinoids and compounds found in FSO. Commonly used methods for isolating CBD from FSO include distillation and column chromatography. Isolation of CBD from FSO yields CBD in a solution which can be evaporated to leave purified CBD isolate crystals or crystalline powder. CBD isolate typically contains 99% or greater CBD purity, and essentially no THC.

After FSO and CBD isolate has been obtained by any of a number of different methods, it is critical to test the FSO and CBD isolate for CBD content 305. Analysis of FSO and CBD isolate is typically done using high-performance liquid chromatography (HPLC), or gas chromatography (GC).

Exemplary test results are provided below in the Examples. Preferably, FSO as used in the formulations contains less than 0.3% THC. The final amount of THC in the formulations will contain less than the amount of THC in the FSO alone. Accordingly, the amount of THC in the presently disclosed formulations preferably will range in an amount of trace THC that is not detected within the limits of the HPLC analysis up to a maximum amount of less than 0.3% THC; from 0.05% to less than 0.25% THC; from 0.05% to less than 0.2% THC, and from 0.05% to less than 0.15% THC.

After the amounts of CBD in FSO and CBD isolate are determined, the FSO and CBD isolate are combined to yield a desirable amount of CBD in a given formulation 310. The amount of CBD in a given application, such as tinctures, creams or lotions, balms, edible treats, and the like in the presently disclosed formulations is obtained by combining an amount of CBD contained in FSO and augmenting it with CBD isolate. For example, a tincture having 1000 mg CBD in a 1-ounce final volume might contain 700 mg of CBD from FSO (70%) and 300 mg CBD from CBD isolate (30%). The amount of CBD will slightly vary from one preparation to another of FSO. It is therefore essential that the amounts of CBD in FSO and CBD isolate are determined by analytical testing, preferably HPLC, so that the FSO and CBD isolate can be combined to yield the desired amount of CBD in a given formulation. Likewise, it is essential to determine the amount of THC in FSO, so that the amount of THC in a given formulation of FSO and CBD isolate can be minimized to a desirable level. For example, if a preparation of FSO contains a total amount of THC of 0.28%, a formulation having a final amount of 0.2% THC might contain 71% FSO in a final volume and the appropriate amount of CBD isolate to achieve both the desired amounts of THC and CBD in the final formulation.

Another aspect that will influence the amount of FSO in a given formulation of FSO and CBD isolate is the taste of the formulation for oral consumption/applications. The taste is empirically determined by taste testing 315. For example, based on CBD and THC content, a starting point for a given formulation might be 70% FSO and 30% CBD isolate. However, if those amounts yield an unacceptable poor tasting formulation due to other components in the FSO, the amount of FSO and CBD isolate might be adjusted 325 to levels of 65% FSO and 35% CBD isolate, or 60% FSO and 40% CBD isolate, to arrive at a total level of desired CBD in a formulation, such as 500 mg or 1000 mg.

In view of the factors of CBD content, THC content, and taste, the formulations disclosed herein will contain a range of concentrations/percentages of FSO and CBD isolate to yield a desired level of CBD content, such as 500 or 1000 mg. Ranges of FSO to CBD isolate in the formulations will range from 55% FSO and 45% CBD isolate, 60% FSO and 40% CBD isolate, 65% FSO and 35% CBD isolate, 70% FSO and 30% CBD isolate, 75% FSO and 25% CBD isolate, 80% FSO and 20% CBD isolate, and all variations that lie between these ranges.

The final amounts of FSO and CBD isolate combined will yield 100% of the final amount of CBD desired for a given formulation. For example, a desired formulation of 1000 mg CBD might contain 70% FSO and 30% CBD isolated to yield a 100% level of 1000 mg CBD in the formulation.

The FSO and CBD isolate combined formulations will be used in a wide array of CBD containing final products that provide CBD medicinal and health benefits. These products include, but are not limited to, orally ingested and topically applied CBD products, such as, but not limited to, tinctures, capsules, creams and lotions, roll ons, balms, lip balms, bath salts/bombs, soaps, and pet/animal applications, such as tinctures, butters, and edible chews.

In one embodiment, the FSO and CBD isolate formulations will be used in an orally applied tincture. Such a tincture will typically contain 500 mg or 1000 mg of CBD in a 1- or 2-oz final product. For example, a 1,000 mg tincture might contain 700 mg CBD from FSO and 300 mg CBD isolate in a final volume of 1 ounce. The 1000 mg tincture described may be prepared as a part of a larger batch wherein 260 g of CBD Isolate is mixed with 340 g FSO, 19 kg of MCT fractionated coconut oil, and 90-140 mL of a desired flavoring. Similarly, a 500 mg tincture described above may also be prepared as part of a larger batch containing 120-140 g CBD isolate, 180 g FSO, 14 kg of MCT oil, and 140 mL of desired flavoring. As described above, the amount of FSO and CBD isolate in an orally delivered tincture will vary, depending on the concentration of CBD in the FSO and CBD isolate, THC levels in the FSO, and the flavor/taste profile of the formulation. Tinctures can contain various constituents, such as MCT (medium chain triglyceride) oil, grapeseed oil, hempseed oil, a flavoring agent or oil (such as mint, peppermint, berry, cinnamon, etc.), a terpene blend, and other constituents as known in the art. In a preferred embodiment, the final volume of a tincture will include FSO and CBD isolate that has been homogenized in a carrier oil, such as MCT oil. After homogenization of the FSO and CBD in MCT oil, for example, the final volume of the tincture can be obtained by adding more MCT oil to the desired final volume.

In another embodiment, the FSO and CBD isolate formulations disclosed herein will be used in a topically applied formulation, such as a cream, lotion, or roll-on product. A cream, for example, might contain 500 mg or 1000 mg CBD in a 1- or 2-oz cream, respectively, that is applied to a person's skin for localized pain relief. The CBD is derived from a combination of FSO and CBD isolate, such as 67% FSO and 33% CBD isolate. Creams or lotions for topical skin application can additionally contain any of a number of well-known components, such as any of an array of butters (mango butter, shea butter, etc.), oils (coconut oil, almond oil, lavender oil, jojoba oil, rosemary oil, pomegranate oil, etc.), and the like.

In a further embodiment, FSO and CBD formulations can be used in bath salts and bombs. For example, a bath salt or bomb product might contain 50 or 75 mg CBD derived from 72% FSO and 28% CBD isolate. In addition to an FSO and CBD formulation, such products may contain any of well-known bath salt or bomb components or ingredients, such as sodium bicarbonate, citric acid, Epson salts, corn flour, coconut oil, mica colorant, sodium lauryl sulfoacetate, polysorbate 80, topical oils (such as organic peppermint oil, rosemary oil, lemongrass oil, lavender oil, orange oil, and the like), and other commonly used bath salts or bomb ingredients.

In yet another embodiment, the combination FSO and CBD isolate formulations disclosed herein can be used in soap formulations for pain relief, stress relief, hydration, and other purposes. For example, 100 or 200 mg CBD from 69% FSO and 31% CBD isolate can be formulated into a 5- or 10-ounce bar of soap. In addition to CBD, such soaps may contain any of a number of commonly used soap ingredients, including, but not limited to, Nag Champa fragrance, olive oil, coconut oil, palm oil, sodium hydroxide, castor oil, sodium lactate, and other commonly used soap ingredients.

Other embodiments utilizing the FSO and CBD isolate formulations include animal and pet products. Tinctures intended for pets, horses and other animals can contain, for example, 500 or 1000 mg CBD in a 1- or 2-ounce product. The CBD in these products will be derived from FSO and CBD isolate, such as 70% FSO and 30% CBD. Pet or animal tinctures additionally may contain any of a number of other ingredients, such as MCT oil, fish oil, and other pet/animal-friendly oral ingredients.

Another pet or animal embodiment is edible chews that contain CBD. Chews intended for animals include treats infused with, for example, 2, 4, or 8 mg of CBD per chew. The treats will be infused with an FSO and CBD isolate formulation, such as an exemplary formulation of 65% FSO and 35% CBD isolate. Treats that are infused with FSO and CBD isolate formulations will contain any of a number of commonly used ingredients in edible pet chews. Such ingredients include, but are not limited to, flour (preferably rice or brown rice flour), pumpkin, peanut butter, eggs, honey, meat (such as bacon, beef, chicken, pork, etc.), meat flavoring agents, and so on.

In yet another embodiment, the combination FSO and CBD isolate formulations disclosed herein can be used in a butter intended for oral consumption for pain relief, stress relief, hydration, and other purposes. Servings of such butters may be sold in serving sizes providing 500 mg of CBD each. Such serving sizes may be prepared as part of a larger batch, which may include 6 lbs shea butter, 6 lbs mango butter, 6 lbs coconut oil, 70 mL jojoba oil, 70 mL almond oil, 70 mL lavender E oil, 70 mL rosemary E oil, 5 mL vitamin E concentrate, 8 oz of tapioca starch, 120 g FSO, and 100 g CBD isolate. Butters may be prepared using non-decarboxylated FSO.

While present embodiments have been described as having configurations disclosed herein, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

The following examples illustrate certain aspects of present embodiments but are not intended to limit in any manner the scope of the invention.

Example I

HPLC Analysis of FSO

FSO CBD oil was obtained from industrial hemp via ethanol extraction. The FSO was analyzed by HPLC to determine the levels of cannabinoids in the FSO. The results obtained were as follows:

| Summary of results: | |
| --- | --- |
| Total THC | 2.382% |
| Total CBD | 52.933% |
| Total THC + CBD | 55.31% |
| Total cannabinoids | 56.184 |

-continued

| % Detailed results: | |
|---|---|
| Cannabinoid | Concentration |
| CBC | ND |
| CBD | 52.933% |
| CBDA | ND |
| CBG | 0.869% |
| CBGA | ND |
| CBN | ND |
| THC-8 | ND |
| THC-9 | 2.382% |
| THCA | ND |
| THCV | ND |

ND = Not detected. The limit of quantitation was 0.40%.
Potency Conversion:
Total THC = [THCA × 0.877] + [Δ9THC] Total CBD = [CBDA × 0.877] + [CBD]
Total Cannabinoids = Sum(All Cannabinoids)

Example II

HPLC Analysis of CBD Isolate

CBD isolate was analyzed by HPLC to determine the levels of cannabinoids in the FSO. The results obtained were as follows:

| Summary of results: | |
|---|---|
| Total TCH | ND |
| Total CBD | 97.27% |
| Total THC + CBD | 97.27% |
| Total cannabinoids | 97.2 |

| 7% Detailed results: | |
|---|---|
| Cannabinoid | Concentration |
| CBC | ND |
| CBD | 97.27% |
| CBDA | ND |
| CBG | ND |
| CBGA | ND |
| CBN | ND |
| THC-8 | ND |
| THC-9 | ND |
| THCA | ND |
| THCV | ND |

ND = Not detected. The limit of quantitation was 0.40%.
Potency Conversion:
Total THC = [THCA × 0.877] + [Δ9THC] Total CBD = [CBDA × 0.877] + [CBD]
Total Cannabinoids = Sum(All Cannabinoids)

Example III

HPLC Analysis of a CBD Tincture

A formulation of CBD tincture was analyzed by HPLC to determine the levels of cannabinoids in the tincture. The results obtained were as follows:

| Cannabinoid | Concentration |
|---|---|
| CBC | 0.935 mg/g |
| CBD | 25.315 mg/g |
| CBDA | 1.933 mg/g |
| CBG | ND |
| CBGA | ND |
| CBN | ND |
| THC-8 | ND |
| THC-9 | ND |
| THCA | ND |
| THCV | ND |

ND = Not detected. The limit of quantitation was 0.40 mg/g.
Potency Conversion:
Total THC = [THCA × 0.877] + [Δ9THC] Total CBD = [CBDA × 0.877] + [CBD]
Total Cannabinoids = Sum(All Cannabinoids)

Example IV

HPLC Analysis of a CBD Tincture

A formulation of peppermint flavored CBD tincture containing 1000 mg CBD was analyzed by HPLC to determine the levels of cannabinoids in the tincture. The results obtained were as follows:

| Cannabinoid | Concentration |
|---|---|
| CBC | ND |
| CBD | 26.892 mg/g |
| CBDA | 4.954 mg/g |
| CBG | ND |
| CBGA | ND |
| CBN | ND |
| THC-8 | ND |
| THC-9 | ND |
| THCA | ND |
| THCV | ND |

ND = Not detected. The limit of quantitation was 0.40 mg/g.
Potency Conversion:
Total THC = [THCA × 0.877] + [Δ9THC] Total CBD = [CBDA × 0.877] + [CBD]
Total Cannabinoids = Sum(All Cannabinoids)

Example V

Analysis of a CBD Tincture

A 28.5 g formulation of berry flavored CBD tincture containing CBD was analyzed to determine the levels of cannabinoids in the tincture. The results obtained were as follows:

| Cannabinoid | Concentration |
|---|---|
| CBC | 53.6 mg/28.5 g |
| CBD | 852 mg/28.5 g |
| CBDA | 1.07 mg/28.5 g |
| CBDV | 4.08 mg/28.5 g |
| CBG | 7.67 mg/28.5 g |
| CBGA | ND |
| CBN | 2.51 mg/28.5 g |
| THC-8 | ND |
| THC-9 | 52.2 mg/28.5 g |
| THCA | ND |
| THCV | 2.53 mg/28.5 g |

ND = Not detected. The limit of quantitation was 0.40 mg/g.
Potency Conversion:
Total THC = [THCA × 0.877] + [Δ9THC] Total CBD = [CBDA × 0.877] + [CBD]
Total Cannabinoids = Sum(All Cannabinoids)

Example VI

Analysis of a CBD Tincture

A 28.5 g formulation of mint flavored CBD tincture containing CBD was analyzed to determine the levels of cannabinoids in the tincture. The results obtained were as follows:

| Cannabinoid | Concentration |
| --- | --- |
| CBC | 53.3 mg/28.5 g |
| CBD | 866 mg/28.5 g |
| CBDA | 1.55 mg/28.5 g |
| CBDV | 4.10 mg/28.5 g |
| CBG | 6.95 mg/28.5 g |
| CBGA | ND |
| CBN | 2.56 mg/28.5 g |
| THC-8 | ND |
| THC-9 | 51.9 mg/28.5 g |
| THCA | ND |
| THCV | 1.13 mg/28.5 g |

ND = Not detected. The limit of quantitation was 0.40 mg/g.
Potency Conversion:
Total THC = [THCA × 0.877] + [Δ9THC] Total CBD = [CBDA × 0.877] + [CBD]
Total Cannabinoids = Sum(All Cannabinoids)

Example VII

Analysis of FSO

FSO CBD oil was obtained from industrial hemp via ethanol extraction. The FSO was analyzed to determine the levels of cannabinoids in the FSO. The results obtained were as follows:

| Summary of results: | |
| --- | --- |
| Total THC | 8.17% |
| Total CBD | 52.3% |
| Detailed results: | |

| Cannabinoid | Concentration |
| --- | --- |
| CBC | 3.76% |
| CBCA | 4.52% |
| CBD | 21.2% |
| CBDA | 35.5% |
| CBG | 0.5% |
| CBGA | 0.735% |
| CBN | 0.222 |
| THC-8 | ND |
| THC-9 | 5.1% |
| THCA | 3.5% |
| THCV-A | 0.233% |
| THCV | 0.134% |

ND = Not detected. The limit of quantitation was 0.40%.
Potency Conversion:
Total THC = [THCA × 0.877] + [Δ9THC] Total CBD = [CBDA × 0.877] + [CBD]
Total Cannabinoids = Sum(All Cannabinoids)

Example VIII

Analysis of CBD Formulation in Butter

The above described CBD formation was incorporated into a butter. The butter was analyzed to determine the levels of cannabinoids in the product. The results obtained were as follows:

| Summary of results: | |
| --- | --- |
| Total THC | 0.136% |
| Total CBD | 1.75% |
| Detailed results: | |

| Cannabinoid | Concentration |
| --- | --- |
| CBC | 59.4 mg/27 g |
| CBD | 359 mg/27 g |
| CBDA | 130 mg/27 g |
| CBDV | 2.61 mg/27 g |
| CBG | 7.8 mg/27 g |
| CBGA | 2.66 mg/27 g |
| CBN | 1.6 mg/27 g |
| THC-8 | ND |
| THC-9 | 26.5 mg/27 g |
| THCA | 11.6 mg/27 g |
| THCV | ND |

ND = Not detected. The limit of quantitation was 0.40%.
Potency Conversion:
Total THC = [THCA × 0.877] + [Δ9THC] Total CBD = [CBDA × 0.877] + [CBD]
Total Cannabinoids = Sum(All Cannabinoids)

Example IX

Empirical Estimate of FSO/CBD Isolate Mixture

The approximate cannabinoid content of the CBD formulation disclosed herein is estimated based upon the cannabinoid content FSO and CBD Isolate and the ratios of FSO to CBD Isolate disclosed herein.

| Cannabinoid Content of FSO/CBD Isolate Formulation | | | | | | |
| --- | --- | --- | --- | --- | --- | --- |
| Cannab- | Ex. VII | Ex. II | FSO to CBD Isolate Ratio | | | |
| inoid | FSO | CBD Iso. | 55/45 | 60/40 | 70/30 | 80/20 |
| CBD | 52.30% | 97.27% | 72.54% | 70.29% | 65.79% | 61.29% |
| THC | 8.17% | 0.00% | 4.49% | 4.90% | 5.72% | 6.54% |
| CBC | 8.28% | 0% | 4.55% | 4.97% | 5.80% | 6.62% |
| CBG | 1.24% | 0% | 0.68% | 0.74% | 0.87% | 0.99% |
| CBN | 0.22% | 0% | 0.12% | 0.13% | 0.15% | 0.18% |

What is claimed is:

1. A cannabidiol (CBD) formulation comprising full spectrum cannabidiol oil (FSO), and cannabidiol isolate (CBD isolate), wherein the FSO and CBD isolate contribute an amount of CBD to the formulation, wherein the amount of CBD is 60-75% (wt.) of the formulation, and wherein the formulation contains less than 7% (wt.) tetrahydrocannabinol (THC).

2. The cannabidiol formulation of claim 1 further comprising cannabichromene (CBC).

3. The cannabidiol formulation of claim 2 further comprising cannabigerol (CBG).

4. The cannabidiol formulation of claim 2 further comprising cannabichromene (CBC), wherein the CBC is at least 3% (wt.) of the formulation.

5. The cannabidiol formulation of claim 4 further comprising cannabigerol (CBG), wherein the CBG is at least 0.5% (wt.) of the formulation.

6. The cannabidiol formulation of claim 1 wherein the formulation is incorporated into a tincture, capsule, lotion, bath sat, lip balm, edible chew, butter, bath bomb, or animal treat.

7. The cannabidiol (CBD) tincture of claim 6 wherein the tincture contains less than 0.25% (wt.) tetrahydrocarinabinol (THC).

8. The cannabidiol (CBD) tincture of claim 6 wherein the tincture contains less than 0.2% (wt.) tetrahydrocannabinol (THC).

9. The cannabidiol (CBD) tincture of claim 6 wherein the tincture contains less than 0.15% (wt.) tetrahydrocannabinol (THC).

10. The cannabidiol (CBD) tincture of claim 6 further comprising at least 0.1% (wt.) cannabichromene (CBC).

11. The cannabidiol (CBD) tincture of claim 6 further comprising at least 0.02% (wt.) cannabigerol (CBG).

12. The cannabidiol (CBD) tincture of claim 6 wherein the tincture has a berry or mint flavor.

13. A method for the production of the cannabidiol (CBD) formulation of claim 1 the method comprising:
   (a) obtaining an amount of a full spectrum cannabidiol oil (FSO) containing CBD;
   (b) obtaining an amount of a cannabidiol isolate (CBD isolate) containing CBD;
   (c) determining by analytical testing the CBD content of the FSO;
   (d) determining by analytical testing the CBD content of the CBD isolate; and
   (e) mixing the FSO and the CBD isolate to produce the formulation.

14. The method of claim 13 wherein the analytical testing method is high performance liquid chromatography (HPLC) or gas chromatography (GC).

15. The method of claim 13 further comprising determining the flavor profile of the formulation.

16. The method of claim 13 further comprising increasing the amount of CBD isolate relative to the amount of FSO to improve the flavor profile.

17. The method of claim 13 further comprising incorporating the CBD formulation into a tincture, capsule, lotion, bath salt, lip balm, edible chew, butter, bath bomb, or animal treat.

* * * * *